United States Patent
Gutierrez-Rocca et al.

(10) Patent No.: US 6,491,950 B1
(45) Date of Patent: Dec. 10, 2002

(54) CONTROLLED RELEASE PHARMACEUTICAL COMPOSITION

(75) Inventors: Jose Gutierrez-Rocca, Miami, FL (US); Josephine Dunne, Plantation, FL (US)

(73) Assignee: Kos Pharmaceuticals, Inc., Miami, FL (US)

( * ) Notice: Subject to any disclaimer, the term of this patent is extended or adjusted under 35 U.S.C. 154(b) by 72 days.

(21) Appl. No.: 09/649,776

(22) Filed: Aug. 29, 2000

Related U.S. Application Data
(60) Provisional application No. 60/223,655, filed on Aug. 7, 2000.

(51) Int. Cl.⁷ .............................. A61K 9/14; A61K 9/52; A61K 9/48
(52) U.S. Cl. ...................... 424/486; 424/488; 424/457; 424/451
(58) Field of Search .................................. 424/489, 486, 424/451, 450, 480, 488, 473, 455, 456, 457

(56) References Cited

U.S. PATENT DOCUMENTS

| | | | |
|---|---|---|---|
| 4,844,905 A | | 7/1989 | Ichikawa et al. |
| 5,645,856 A | * | 7/1997 | Lacy et al. .................. 424/455 |
| 6,190,692 B1 | * | 2/2001 | Busetti et al. .............. 424/451 |

* cited by examiner

Primary Examiner—Thurman K. Page
Assistant Examiner—Blessing Fubara
(74) Attorney, Agent, or Firm—Frommer Lawrence & Haug LLP

(57) ABSTRACT

A controlled release pharmaceutical formulation is disclosed. The formulation comprises a construct having a matrix of a material selected from the group comprising (a) a high melting point fatty acid ester, (b) an oil, (c) a polymeric cellulose derivative and (d) a mixture of any of the foregoing. Associated with the matrix is a selected medicament. Preferably, the matrix comprises at least two of the aforementioned materials or components.

39 Claims, 12 Drawing Sheets

CONTROLLED RELEASE PHARMACEUTICAL COMPOSITION

This application claims the benefit of U.S. application Ser. No. 60/223,655 filed on Aug. 7, 2000, which are incorporated hereinto by reference in its entirety.

BACKGROUND OF THE INVENTION

One of the most frequently utilized methods to extend the duration of drug action in the body is by modification of the pharmaceutical dosage form. This is usually achieved with single or multicomponent matrix systems such as granules, pellets, tablets or combination of the above where the drug delivery is mainly controlled by diffusion or erosion mechanisms.

Another commonly used procedure to sustain or control the rate of drug release is by utilizing polymer coating technology. Polymers with pH dependent or independent properties are coated onto the different dosage forms utilizing fluid bed or conventional coating equipment.

The delivery systems described above, traditionally have been used to manufacture many of the available pharmaceutical dosage forms in the market. However, for drugs that present a low melting point or are metastable at room temperature the only available solid oral unit dosage form has been the soft gelatin capsule.

Soft gelatin encapsulation is rather a complex process and usually requires the services of an outside contractor. However, many pharmaceutical companies would prefer to keep development activities in house for reason of confidentiality and control over the development process. With the new advances in pharmaceutical equipment technology it is now possible to formulate drug substances into semisolid, liquid or paste-like form for filling into hard-shell two piece capsules. This type of formulation technology demonstrated an alternative for the difficult to manufacture soft gelatin technology and the ability to maintain the development activities in-house.

There are several advantages that can be obtained by formulating drugs in liquids and/or semisolid (molten) formulations to be filled into hard shell two piece capsules. These are the ability to formulate with low melting point materials, low-dosed or highly potent drugs, compounds that are oxygen- or moisture sensitive, and for drugs that require bioavailability enhancement.

Many of the liquid formulations in hard-shell capsules provide an immediate or fast release. This is usually achieved as a result of the immediate release of the contents due to the fast disintegration time of the gelatin at body temperature. Other formulations utilize sustained release liquid-filled release capsules utilizing thermosoftening matrices. The excipients most frequently utilized are the Gelucires®, since they are avialable as semisolids with a a wide range of melting points and HLB values. This variety allows flexibility in mixing, adequate filling viscosity, different degrees of bioavailability enhancement and a sustained drug release from the semisolid matrix.

High melting glycerides have frequently been used as lubricants when formulating tablets or capsules. Lubricants have a great effect on the aspect of the finished product and the ejection of the tablet out of the die is improved. Lubricants are usually hydrophobic substances and when used in high amount can alter the desegregation time of the tablet thus delaying the bioavailability of the active ingredient.

The incorporation of lubricants (waxes, HMG) into tablet matrices have been a popular method to prolong drug release. For example, sustained release acetaminophen tablets with glyceryl behenate, Klucel HXF, hydroxy propyl cellulose (HPC), a swellable water-soluble polymer, and Carbopol® 934, a crosslinked polymer has been prepared. It was observed that all tablets containing a sustained release agent exhibited some degree of prolonged drug release in vivo as compared to regular tablets. It was also noted that from all sustained release agents evaluated glyceryl behenate provided the slowest release.

Glyceryl behenate as a potential controlled release wax matrix in spheres and tablets has been evaluated (10, 30 and 50%). At the 10% level no sustained action was observed. However, as the levels of glyceryl behenate increased a significant slower release of the drug was obtained. The result indicated that glyceryl behenate exhibited the potential to create a controlled release matrix.

Sustained release preparations have also been achieved from other high melting glycerides (glycerol palmitostearate and glyceryl monostearate). For example the release of theophylline embedded in a glycerol palmitostearate matrix containing varying amounts of mannitol and/or hydroxypropyl methyl cellulose 4000 (HPMC) was evaluated. The release of theophylline was modulated by varying the fraction of HPMC and/or mannitol used. When both HPMC and mannitol were used the matrix system developed followed a first-order dissolution release.

In general, natural, synthetic and/or semi-synthetic polymers such as cellulose or acrylics derivatives, have been used in high quantities (>10%) to retard the release of many pharmaceutical active ingredients. Such polymers are not usually recommended to be utilized in small quantities to retard the release of API.

SUMMARY OF THE INVENTION

A controlled release pharmaceutical formulation is disclosed. The formulation comprises a matrix construct of a component selected from a high melting point fatty acid ester, an oil, a polymeric cellulose derivative, and a mixture of any of the foregoing, having a selected medicament associated therewith.

DETAILED DESCRIPTION OF THE INVENTION

Figure 1:
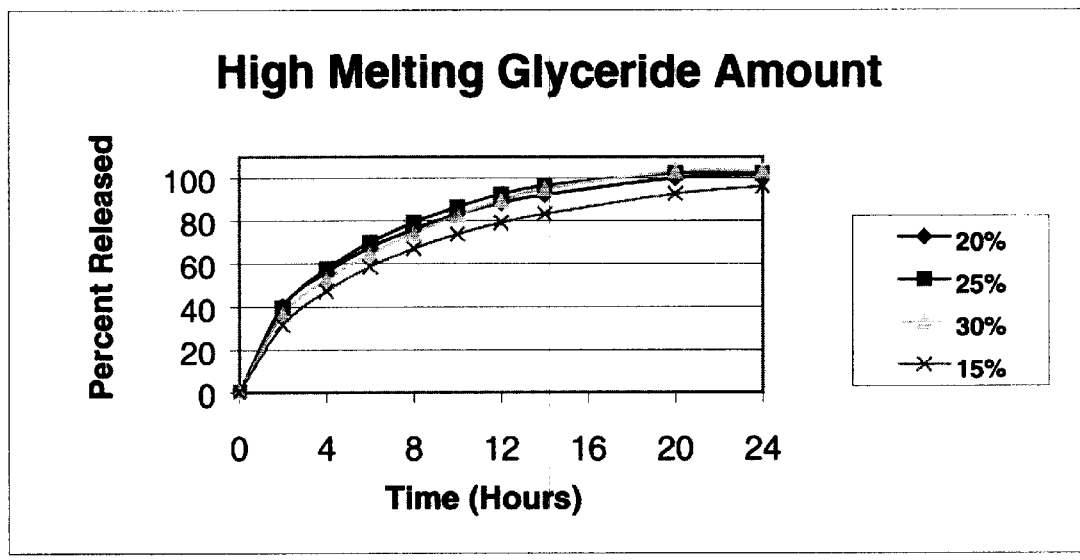
FIG. 1 is a graphical representation of the release of medicament in EXAMPLE 1 in terms of percent released with time.

The present invention relates to a sustained or modulated pharmaceutical formulation comprising (1) a selected medicament or drug, (2) a suitable construct with which the drug is associated, i.e. is encapsulated therewithin or being part of the construct. The construct provides a modulated release of the associated, e.g. encapsulated, drug to the body of a patient, e.g. a human being or another animal, when the construct is administered e.g. orally, to the patient.

The formulation is intended to be administered orally to the patient in a dosage form comprising a hard shell capsule filled with the formulation.

Suitable therapeutic medicament categories of drugs or medicaments are those which are water soluble and include cardiovascular drugs, antiallergics, analgesics, bronchdialtors, antihistamines, antitissives, antifungals, antivirals, antibiotics, other pain medicaments, antiinflamatories, etc. Particularly suitable medicaments include a pharmaceutically acceptable acid addition salt of hydroxyzine, a pharmaceutically acceptable acid addition salt of metoprolol, niacin, caffeine, theophylline, a pharmaceutically acceptable acid addition salts of diltiazem, a pharmaceutically acceptable acid addition salt of albuterol, a pharmaceutically acceptable acid addition salt of metformin, a pharmaceutically acceptable acid addition salt of metromidazole, a pharmaceutically acceptable acid addition salt of metochlopramide, a pharmaceutically acceptable acid addition salt of ranitidine, and a pharmaceutically acceptable acid addition salt of captopril.

For purposes of the formulations of this invention, which are intended for incorporation into a hard shell capsule unit dosage form, the biotherapeutic medicament or drug is associated with the construct carrier with which it is destined to be combined. By "associate" or "associated" is meant that the medicament is present as a matrix or a part of the matrix along with the component making up the construct or is encapsulated within the carrier matrix, or is on the surface of the carrier matrix.

A suitable construct is selected. Such a construct is one which will incorporate or encapsulate the selected medicament and provide a controlled or modulated release of the medicament therefrom to the sites of action or application to the patient's body, e.g. to the hepatobiliary receptors of the human being or other animal.

A suitable carrier construct comprises a material or component selected from the group comprising a high melting fatty acid ester, such as for example glyceryl behenate, gyceryl palmitosterate and glyceryistearate; an oil, e.g. corn oil, cottonseed oil, menhaden oil, safflower oil, sesame oil, shark-liver oil, soybean oil, olive oil and wheat germ oil; a cellulosic polymer, e.g. methocel E10, methocel A4M, methocel K15M, ethocell P20, methocel K100LV and methocel K100M, low-substituted hydroxypropyl ether cellulose polymers LH11, LH22, and LH30; and a mixture of any of the foregoing. Preferably, the formulation comprises a mixture of at least two of the foregoing components.

The dosage form comprising a hard shell capsule utilizes the formulation, i.e. the construct or the matrix having the medicament associated therewith. Preferably, the sustained/prolonged release pharmaceutical unit dosage form comprises the matrix or construct formulated from a mixture of the above-described materials or components.

The water soluble medicaments of the formulation and the sustained/prolonged release capsule unit dosage form of the present invention comprise a group of a pharmaceutically active drugs having a solubility greater than 1 gram (g) of drug in about 200 milliliters (ml) of water. Drugs having such a solubility in water are niacin, caffeine and theophylline. Drugs not having a solubility in water greater than about 1 g/200 ml of water may be solubilized by conversion to a pharmaceutically acceptable acid or base addition salt. Preferred pharmaceutically acceptable acid addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, tartaric acid, succinic acid and the like, and salts of tribasic carboxylic acids such as, for example, carboxysuccinic acid, citric acid and the like. Preferred pharmaceutically acceptable basic addition salts include salts of alkali metals, e.g. sodium or potassium; alkaline earth metals, e.g., calcium or magnesium; or complex salts, e.g., ammonium or substituted amonium salts such as mon-, di- or trialkylammonium salts or mono, di- or trihydroxyalkylammonium salts. Some suitable drugs in the form of their pharmaceutically acceptable salts include hydroxyzine hydrochloride, metoprolol tartrate, diltiazem hydrochloride, metaformine hydrochloride, albuterol sulfate, metromidazole hydrochloride, metochlopramide hydrochloride, ranitidine hydrochloride, captopril dihydrochloride, brompheniramine maleate, ranitidine HCl, cimetidine HCl, ferrous sulfate, methoscopolamine bromide, oxeprenolol HCl, etidronate disodium and alendronate sodium.

The high melting fatty acid esters (high melting glycerides) of the formulation and the sustained/prolonged release capsule unit dosage forms of the present invention comprise esters of fatty acids and polyhydric alcohols, such as glycerol, melting at elevated temperatures within the range of from about 50° to about 80° C. The melting points of fatty acid esters of behenic acid (docosanoic acid), palmitostearic acid and stearic acid and glycerol fall within this range and are suitable for the formulations and unit dosage forms of the present invention. Other high melting fatty acid esters, that is, fatty acid esters melting within the range (ca. 50 to ca 80° C.), may be employed in the formulations and dosage forms.

The oils of the formulations and the sustained/prolonged release capsule unit dosage forms of the present invention comprise triglycerides of fatty acids having short (12 to 14 carbon atoms), medium (16 to 18 carbon atoms) and long (18 to 22 carbon atoms) carbon chains and no, or up to 6 double bonds. Exemplary fatty acids are lauric acid (12 carbon atoms, no double bonds), myristic acid (14 carbon atoms, no double bonds), palmitic acid (16 carbon atoms, no double bonds) palmitoleic acid (16 carbon atoms, one double bond), stearic acid (18 carbon atoms, no double bonds), oleic acid (18 carbon atoms, 1 double bond), linoleic acid (18 carbon atoms, 2 double bonds), eicosapentaenoic acid (20 carbon atoms, 5 double bonds ("EPA") and docosahexanoic acid (22 carbon atoms, 6 double bonds), which are found in various animal and vegetable oils listed in the Table below.

TABLE

Super Refined ® Oils and the Associated Typical Fatty Acid Distribution (%)

| Super Refined Product | Myristic | Palmitic | Palmitoleic | Stearic | Oleic | Linoleic | Linolenic | EPA | DHA |
|---|---|---|---|---|---|---|---|---|---|
| Corn | 1 | 10 | 0 | 3 | 30 | 55 | 0 | 0 | 0 |
| Cotton-seed | 1 | 24.5 | 0 | 2.5 | 17 | 55 | <1 | 0 | 0 |
| Menhaden | 8.5 | 23 | 12.5 | 3 | 12.5 | 2 | <1 | 12 | 8.5 |
| Olive | 0 | 11.5 | 1 | 2 | 75 | 9.5 | 0 | 0 | 0 |
| Peanut | 0 | 7.5 | 1 | 4.5 | 62 | 20 | 0 | 0 | 0 |
| Safflower | 0 | 7 | 0 | 3 | 15 | 75 | 0 | 0 | 0 |
| Sesame | 0 | 8 | 0 | 4.5 | 43 | 41 | 0 | 0 | 0 |
| Shark-liver | 2 | 12 | 7 | 4 | 30 | 6 | 5 | 4 | 4 |
| Soybean | 0 | 9 | 0 | 4 | 24 | 52 | 8 | 0 | 0 |
| Wheat-germ | 0 | 13.5 | 0 | 3.5 | 19 | 54.5 | 7 | 0 | 0 |

The cellulosic polymers of the formulations and sustained/prolonged release capsule unit dosage forms of the present invention comprise glucose polysaccharide ethers having multiple glucose units and methyl, ethyl, hydroxyethyl, hydroxypropyl or hydropropyl methyl substitution. Exemplary cellulosic polymers having methylether substitution are the methocels, i.e., methocel E10, methocel A4M, methocel K15M, methocel K100LV and methocel K100M, and the ethocels, for example, ethocel P20 and low-substituted hydroxypropyl ether cellulose polymers LH11, LH22 and LH30.

Surfactants which may optionally be employed with the formulations and sustained/prolonged release capsule unit dosage forms of the present invention, comprise polysorbates, such as ethers of polyoxyethylene sorbitan and fatty acids. Exemplary surfactants are polysorbate 80 and polyoxyethylene 20 sorbitan monoleate, polyoxyxethylene alkyl ethers of the Brig- or Volpo series, Cremophor RH, Cremophor E1, polyoxyethylene sorbitant fatty acid esters of the Tween- or Crillet series, polyoxyethylene stearates of the Cerosynt- or Myrj series, lecithin, poloxamers, d-2-tocophenyl polyethylene glycol 1000 succinate (Vitamine E TPGS) and saturated polyglycolized glycerides (Labrosol, Labrafile and Gelucires), polysorbate 80 being preferred.

The release of the active ingredient or drug of the pharmaceutical unit dosage forms of the present invention is sustained over a prolonged period of about 24 hours. The sustained release of the water soluble medicament from a hard shell capsule is dependent upon the type and amount of medicament, the high melting fatty acid ester, cellulose polymer and a surfactant (if employed). Generally, salts of the water soluble medicaments are released faster than unionized water soluble medicaments. For example, hydroxyzine hydrochloride and metoprolol tartrate are released faster than niacin or caffeine.

The most preferred formulation comprises a water soluble medicament, and a mixture comprising glyceryl behenate as the fatty acid ester, an oil, a cellulosic polymer such as for example, a methyl or ethyl ether of a cellulose, e.g., a methocel or an ethocell, and polysorbate 80 surfactant.

Optionally, pharmaceutically acceptable excipients, compatible with the requirements for filling the capsules that the formulation be in the fluid state, i.e., a liquid or semi solid, at the filling temperature, may be included in the formulation. Such excipients comprise a surfactant, such as for example polysorbate 80; stabilizers/antioxidants, such as for example butylated hydroxytoluene, propyl gallate, vitamine E, ascorbic acid and ethylene diamine tetraacetic acid; solubilizers, such as for example N-methyl-2-pyrrolidone, citrate esters, e.g., Citroflex 2, acetylated monoglycerides, e.g., Triacetin and Mygliols; viscosity modifiers, such as for example polyethylene glycols, e.g. PEG, and silica derivatives, e.g., silicon dioxide; and fillers such as for example hydrocarbons, e.g., paraffin and mineral oil. Preferably, combined with the component or components of the carrier and the drug is a surfactant, such as polysorbate 80.

The release of water soluble medicaments from the unit dosage formulation generally depends on the type and amount of the high melting fatty acid in the formulation and varies substantially with the type and amount thereof. For example, the release of hydroxyzine hydrochloride from a formulation of the salt over a prolonged period of about 24 hours, is fastest with Precirol AT05 slowest with Compritol 888/WL 2155, and intermediate with Compritol 888. The release of hydroxyzine hydrochloride from a formulation of the salt is moderately faster as the amount of higher fatty acid ester in the formulation is increased over a small range and then levels off.

The type of oil used in the formulation has essentially no effect on the release of the water soluble medicament over the prolonged 24 hour period. For example, the release of hydroxyzine hydrochloride from a formulation containing peanut, corn, sesame or olive oil is sustained at the same level over the period.

The release of water soluble medicament from a unit dosage formulation is markedly dependent on the type and amount of the cellulosic polymer. For example, hydroxyzine hydrochloride is released considerably faster from a formulation of Methocel K15M than Ethocel P20. Similarly, caffeine is released from a unit dosage formulation faster when the formulation contains Methocel K100M than Ethocel P20, and niacin is released faster from a formulation containing Methocel E10P than from a formulation devoid of the cellulosic polymer.

If employed, the release of the water soluble medicament from a pharmaceutical unit dosage formulation depends not only on the type of surfactant, but also on the amount thereof. For example, the release of niacin from a formulation containing polysorbate 80 is faster the higher the level of the surfactant above a level of about 5.0% of the total amount of the formulation.

The formulations of the water soluble medicaments of the present invention are useful for encapsulation in hard shell capsules for oral administration for the treatment of various diseases and disorders, for example, hydroxyzine hydrochloride as an anxiolytic or antihistamine, metoprolol tartrate as an antihypertensive or anti-anginal agent, niacin (nicotinic acid) as a vitamin enzyme cofactor, caffeine as a central nervous system stimulant, theophylline as a bronchodilator, diltiazem hydrochloride as an anti-anginal agent, albuterol as a bronchodilator, metronidazole as an antibacterial, metochlopramide as an anti-emetic, and captopril as an antihypertensive. The drugs are readily available from commercial suppliers.

The high melting fatty acid esters, the oils, the cellusic polymers and surfactants and other excipients of the formulations of the present invention suitable for encapsulation in hard shell capsules are generally available from commercial sources. The water soluble medicaments are also commercially available. For example, hydroxyzine hydrochloride is available from Spectrum, (Gardena, Calif.); metoprolol tartrate from Moehs, S. A. (Barcelona, Spain); niacin from Lonza (VISP, Switzerland); caffeine from Zetapharm (New York, N.Y.); theophylline from BASF (Wyandotten); and diltiazem from Spectrum, (Gardena, Calif.). Pharmaceutically acceptable acids and bases required for salt formation of water insoluble medicaments are available from suppliers such as Aldrich Chemical Company, Milwaukee, Wis.

The sustained/prolonged release pharmaceutical unit dosage forms are prepared by fluidizing matrix carrier material or components, e.g. a high melting fatty acid ester, an oil, a cellulosic polymer or a mixture of the foregoing, to provide a formulation, to which is added the medicament which dissolves therein, which is then filled into a hard shell capsule, while in the fluid state, and, generally, allowed to solidify in the capsule. The filling of the hard shell capsule is conveniently performed by a capsule filling machine for liquid filling of the type available, for example, from Robert Bosch GmbH, (Hofligen and Kars GKF/L Series), Germany, Harro Hoefleger GmbH, (KFM/L Series), Germany, or Zanasi Nigris SpA (AZ 20/L Series), Italy. The hard shell capsules are generally sealed by one of several methods. The filled capsule may be sprayed with a water alcohol mixture to seal the cap to the body of the container. Alternatively, the cap may be sealed to the body of the container by a bonding process, which entails passing the cap over a revolving wheel immersed in a water gelatin or a cellulose bath and then passing the capsule through a drying chamber to seal the gap between the cap and the body of the capsule with dried gelatin or cellulose. The bonding is generally performed on commercially available machines manufactured by Robert Bosch GmbH and Zanasi Nigris SpA, makers of capsule filling machines, as well as machines manufactured by Eli Lilly and Co., Indianapolis, Ind. Machine performed bonding of the hard shell capsules is preferred.

Empty hard shell capsules are commercially available from the Capsugel Division of Warner-Lambert Co., Morris Plains, N.J., and from Eli Lilly Co., Indianapolis, Ind., in various sizes to accommodate the dosage requirements for the treatment of disease or disorder states. For example, size 0 may be employed for unit dosage forms for potent drug formulations whereas size 000 would be required for a less potent drug, depending on the amounts of the components of the formulation and excipients.

Gelatin and hydroxypropylmethylcellulose (HPMC) capsules may be used as containers for the formulations. Hydroxypropylmethylcellulose capsules are preferred.

The following examples are illustrative and do not define the scope of the invention described and claimed herein.

EXAMPLES

General Example

The sustained/prolonged release formulations of the present invention are generally prepared by heating the matrix component or components until liquid (a melt), usually at the capsule filling temperature (70–90° C.) and adding the water soluble medicament to the melt. The amount of water soluble medicament utilized in all formulations is about 20% of the total amount of the formulation. Size # 0 Hard-Shell hydroxypropylmethylcellulose capsules are utilized since they are heat resistant. In order to assure proper mixing and to reduce the amount of air entrapped with stirring (vortex created), batches containing a minimum of 50 grams are prepared. A general formulation time is illustrated below.

| Ingredients | % | Qty (g) |
| --- | --- | --- |
| Medicament | 20.0 | 10.00 |
| High Melting Glyceride | 25.0 | 12.50 |
| Surfactant | 1.0 | 0.50 |
| Cellulose Polymer | 3.0 | 1.50 |
| Vegetable oil | 51.0 | 25.50 |
| Total | 100.0 | 50.00 |

Example 1

Soybean oil, polysorbate 80, and Compritol 888 in the amounts shown in Table 1 were weighed and placed in a glass beaker. The mixture was heated to 75–80° C. until the contents melted by immersing the beaker into a water bath heated by a Hot-Plate. The melt in the amount shown in Table 1 was stirred with a laboratory mixer fitted with a straight blade propeller to disperse the ingredients and create an homogeneous melt. To the melt, Methocel E 10P was slowly added with heating and stirring. After addition of the Methocel E10P was complete, the melt was cooled to approximately 70° C., and then cooled at approximately 70° C., Hydroxyzine HCl was slowly added, and the melt was stirred until uniform. Capsules size 0 were filled with 500 mg of melt, with a pipette. The filling weights of each capsule were recorded to guarantee consistency. The melt was all regular type maintained at approximately 70° C. during the filling process. The release of the medicament, hydroxyzine hydrochloride, was determined by the method described in Example 13. The results are recorded graphically in FIG. 1 and demonstrate the consistent sustained release over 24 hours of the water soluble hydroxyzine HCl at all levels of the high melting glyceride, Compritol 888, employed.

TABLE 1

| Formula/ Ingredients | 1 | 2 | 3 | 4 |
| --- | --- | --- | --- | --- |
| Hydroxyzine HCl | 20.0 | 20.0 | 20.0 | 20.0 |
| Compritol 888 | 15.0 | 20.0 | 25.0 | 30.0 |
| Methocel E10 P | 3.0 | 3.0 | 3.0 | 3.0 |

TABLE 1-continued

| Formula/Ingredients | 1 | 2 | 3 | 4 |
|---|---|---|---|---|
| Soybean Oil | 61 | 56.0 | 51.0 | 46.0 |
| Polysorbate 80 | 1.0 | 1.0 | 1.0 | 1.0 |

Example 2

Figure 2:
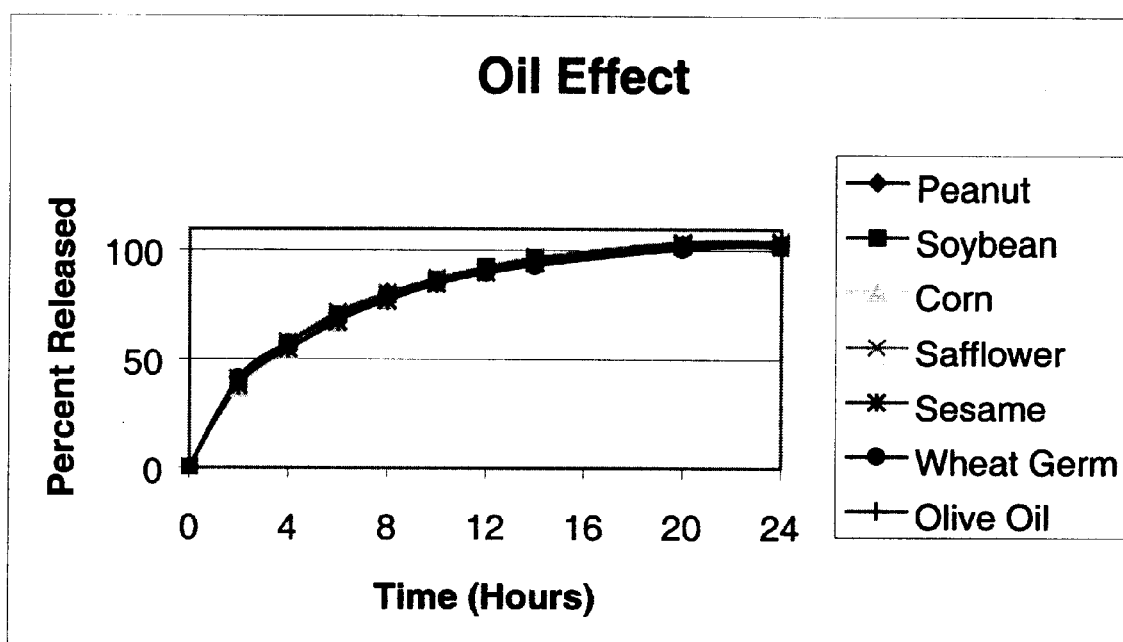
FIG. 2 is a graphical representation of the release of medicament in EXAMPLE 2 in terms of percent released with time.

Following the procedure of Example 1, using the amounts of the components shown in Table 2, hard shell capsules of the formulations were obtained. The capsules were fabricated from hydroxyzine methylcellulose and contained 500 mg of the formulation. The release of the medicament was determined by the procedure of Example 13, and the results are recorded graphically in FIG. 2, showing that the release (dissolution profile) of the medicament is independent of the oil, containing different fatty acids.

TABLE 2

| Formula/Ingredients | 1 | 2 | 3 | 4 | 5 | 6 | 7 |
|---|---|---|---|---|---|---|---|
| Hydroxyzine HCl | 20.0 | 20.0 | 20.0 | 20.0 | 20.0 | 20.0 | 20.0 |
| Compritol 888 | 25.0 | 25.0 | 25.0 | 25.0 | 25.0 | 25.0 | 25.0 |
| Methocel E10 P | 3.0 | 3.0 | 3.0 | 3.0 | 3.0 | 3.0 | 3.0 |
| Peanut Oil | 51.0 | | | | | | |
| Soybean Oil | | 51.0 | | | | | |
| Corn Oil | | | 51.0 | | | | |
| Safflower | | | | 51.0 | | | |
| Sesame oil | | | | | 51.0 | | |
| Wheat Germ | | | | | | 51.0 | |
| Olive oil | | | | | | | 51.0 |
| Polysorbate 80 | 1.0 | 1.0 | 1.0 | 1.0 | 1.0 | 1.0 | 1.0 |

Example 3

Figure 3:
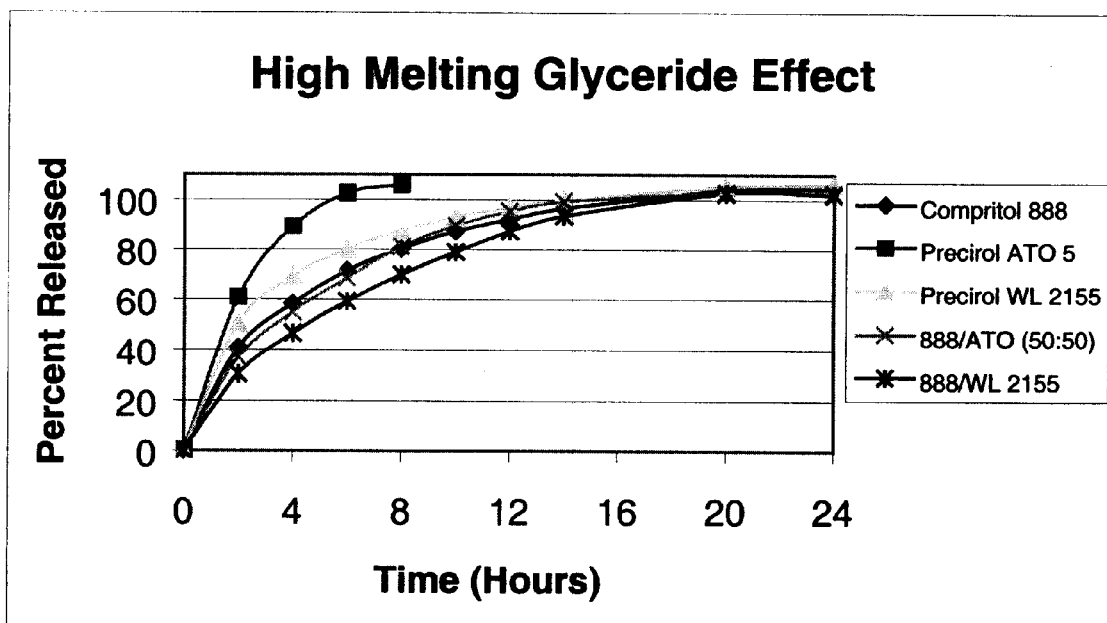
FIG. 3 is a graphical representation of the release of medicament in EXAMPLE 3 in terms of percent released with time.

Following the procedure of Example 1, using the amounts of the components shown in Table 3, hard shell capsules of the formulations were obtained and the release of the medicament was determined by the procedure of Example 13. The results are shown graphically in FIG. 3, and confirm the results of Example 1 that release is sustained consistently over 24 hours with each high melting glyceride. In FIG. 3, 888/ATO(50:50) refers to a mixture of Compritol 888 and Precirol ATO 5 in equal amounts; 888/WL 2155 refers to a mixture of equal parts of Compritol 888 and Precirol WL 2155.

TABLE 3

| Formula/Ingredients | 1 | 2 | 3 | 4 | 5 |
|---|---|---|---|---|---|
| Hydroxyzine HCl | 20.0 | 20.0 | 20.0 | 20.0 | 20.0 |
| Compritol 888 | 25.0 | | | | |
| Precirol ATO 5 | | 25.0 | | | |
| Precirol WL 2155 | | | 25.0 | | |
| Compritol 888/Precirol ATO 5 (50:50) | | | | 25.0 | |
| Compritol 888/Precirol WL (50:50) | | | | | 25.0 |
| Soybean oil | 51.0 | 51.0 | 51.0 | 51.0 | 51.0 |
| Methocel E10 P | 3.0 | 3.0 | 3.0 | 3.0 | 3.0 |
| Polysorbate 80 | 1.0 | 1.0 | 1.0 | 1.0 | 1.0 |

Example 4

Figure 4:
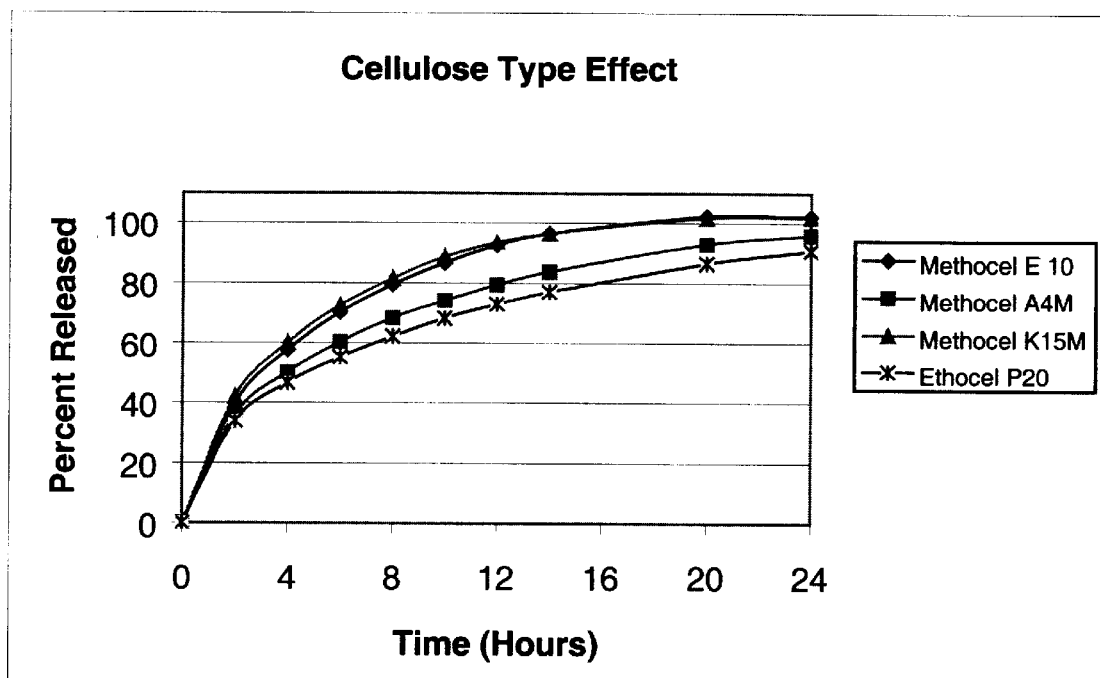
FIG. 4 is a graphical representation of the release of medicament in EXAMPLE 4 in terms of percent released with time.

Following the procedure of Example 1, using the amounts of the components shown in Table 4, hard shell capsules of the formulation were obtained and the release of the medicament was determined by the procedure of Example 13. The results are shown graphically in FIG. 4 and demonstrate that sustained release was achieved over a 24 hour period and further that the release of the medicament is dependent upon the type of the cellulosic polymer, the formulation containing Ethocel P20 polymer having a slower rate than that the Methocell containing polymers, thereby effecting modulation of the sustained release effect.

TABLE 4

| Formula/Ingredients | 1 | 2 | 3 | 4 |
|---|---|---|---|---|
| Hydroxyzine HCl | 20.0 | 20.0 | 20.0 | 20.0 |
| Compritol 888 | 25.0 | 25.0 | 25.0 | 25.0 |
| Methocel E10 P | 3.0 | | | |
| Methocel K15M | | 3.0 | | |
| Methocel A4M | | | 3.0 | |
| Ethocel P20 | | | | 3.0 |
| Soybean Oil | 51 | 51.0 | 51.0 | 51.0 |
| Polysorbate 80 | 1.0 | 1.0 | 1.0 | 1.0 |

Example 5

Figure 5:
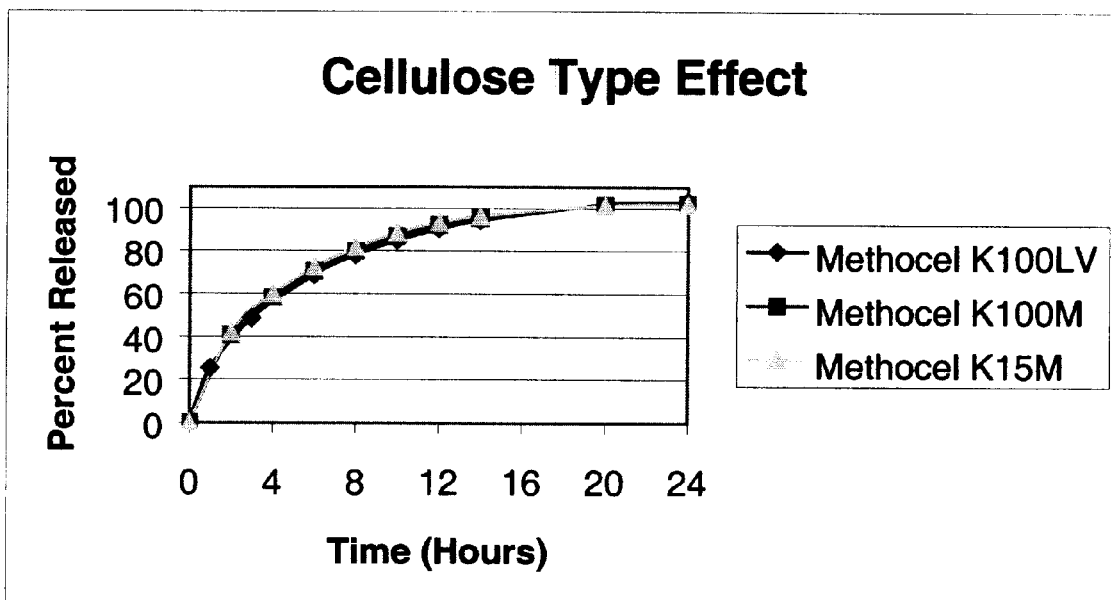
FIG. 5 is a graphical representation of the release of medicament in EXAMPLE 5 in terms of percent released with time.

Following the procedure of Example 1, using the amounts of the components shown in Table 5, hard shell capsules of the formulations were obtained and the release of the medicament was determined by the procedure of Example 13. The results are shown graphically in FIG. 5 and show that sustained release of the medicament is essentially the same over 24 hours for methocels with equivalent chemistry substitution ratios.

TABLE 5

| Formula/Ingredients | 1 | 2 | 3 |
|---|---|---|---|
| Hydroxyzine HCl | 20.0 | 20.0 | 20.0 |
| Compritol 888 | 25.0 | 25.0 | 25.0 |
| Methocel K 15M | 3.0 | | |
| Methocel K100M | | 3.0 | |
| Methocel K10LV | | | 3.0 |
| Soybean Oil | 51 | 51.0 | 51.0 |
| Polysorbate 80 | 1.0 | 1.0 | 1.0 |

Example 6

Figure 6:
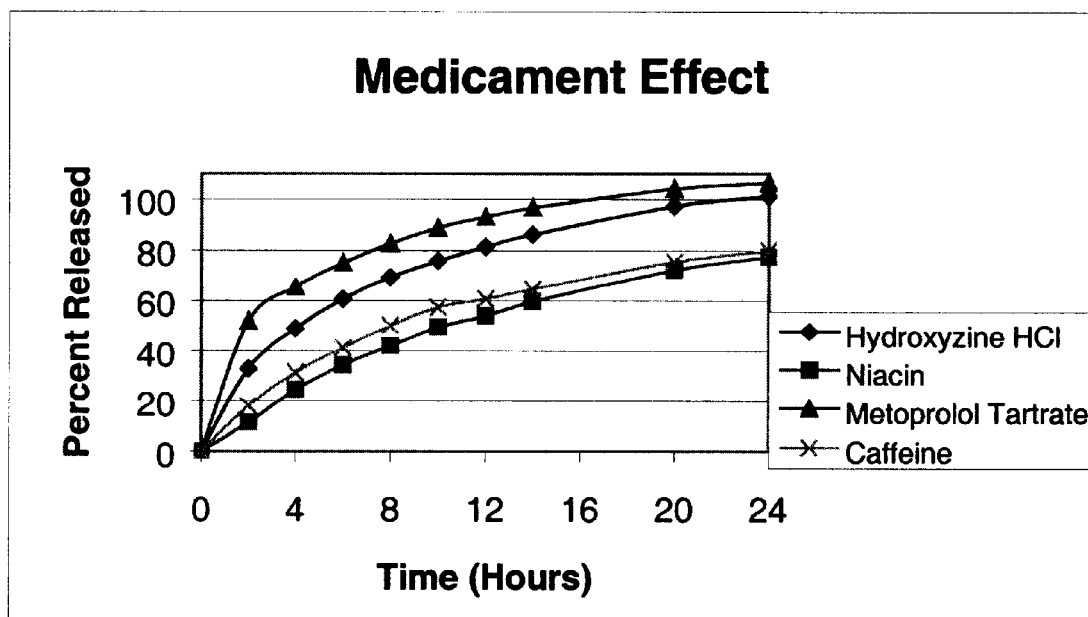
FIG. 6 is a graphical representation of the release of medicament in EXAMPLE 6 in terms of percent released with time.

Following the procedure of Example 1, using the amounts of the components shown in Table 6, hard shell capsules of the formulations were obtained, and the release of the medicament was determined by the procedure of Example 13. The results are shown graphically in FIG. 6. The release is sustained for each medicament, the release being dependent on the type of medicament.

TABLE 6

| Formula/Ingredients | 1 | 2 | 3 | 4 | 5 |
|---|---|---|---|---|---|
| Hydroxyzine HCl | 20.0 | | | | |
| Metoprolol Tartrate | | 20.0 | | | |
| Niacin | | | 20.0 | | |
| Caffeine | | | | 20.0 | |
| Metformin | | | | | 20.0 |
| Methocel E10 P | 3.0 | 3.0 | 3.0 | 3.0 | 3.0 |
| Compritol 888 | 25.0 | 25.0 | 25.0 | 25.0 | 25.0 |
| Soybean Oil | 51 | 51.0 | 51.0 | 51.0 | 51.0 |
| Polysorbate 80 | 1.0 | 1.0 | 1.0 | 1.0 | 1.0 |

Example 7

Figure 7:
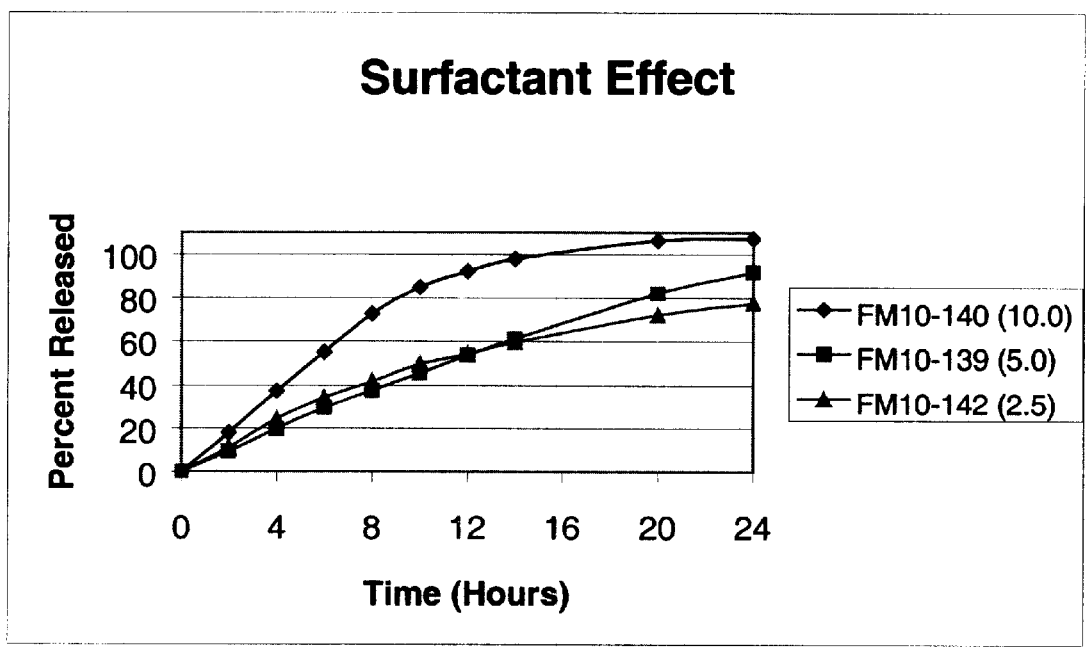
FIG. 7 is a graphical representation of the release of medicament in EXAMPLE 7 in terms of percent released with time.

The formulations were prepared by melting Compritol 888, olive oil and polysorbate 80 in the specified amounts in a beaker. The temperature of the melt was maintained at 75–80° C. by means of a heated plate and water bath. The melt was stirred until it became homogeneous. When the melt was homogeneous and free of any agglomerates Methocel E10 P was slowly added to the melt with continues stirring. The temperature of the melt was then lowered to approximately 70° C. When the melt had cooled to approximately 70° C., Niacin was slowly added, with stirring. The final melt was stirred until uniform. Capsules (# 0) were filled with 500 mg of the melt, utilizing a pipette. The melt immediately solidified in the capsule at room temperature. The release of the medicament was determined by the procedure of Example 13 and is shown graphically in FIG. 7. The release of the medicament is sustained over 24 hours, the release being substantially increased with increasing amounts of the surfactant, i.e., at amounts higher than 5.0%, e.g., 10% of the amounts of surfactant relative to the total of the formulation. In FIG. 7, FM10-140 (10.0), FM10-139 (5.0), FM10-142 (2.5) refer to polysorbate 80 amounts of 10.0, 5.0 and 2.5% of the total amount of the formulation.

TABLE 7

| Formula/Ingredients | 1 | 2 | 3 |
|---|---|---|---|
| Niacin | 20.0 | 20.0 | 20.0 |
| Compritol 888 | 25.0 | 25.0 | 25.0 |
| Methocel E10 P | 3.0 | 3.0 | 3.0 |
| Olive Oil | 49.5 | 47.0 | 42.0 |
| Polysorbate 80 | 2.5 | 5.0 | 10.0 |

Example 8

Figure 8:
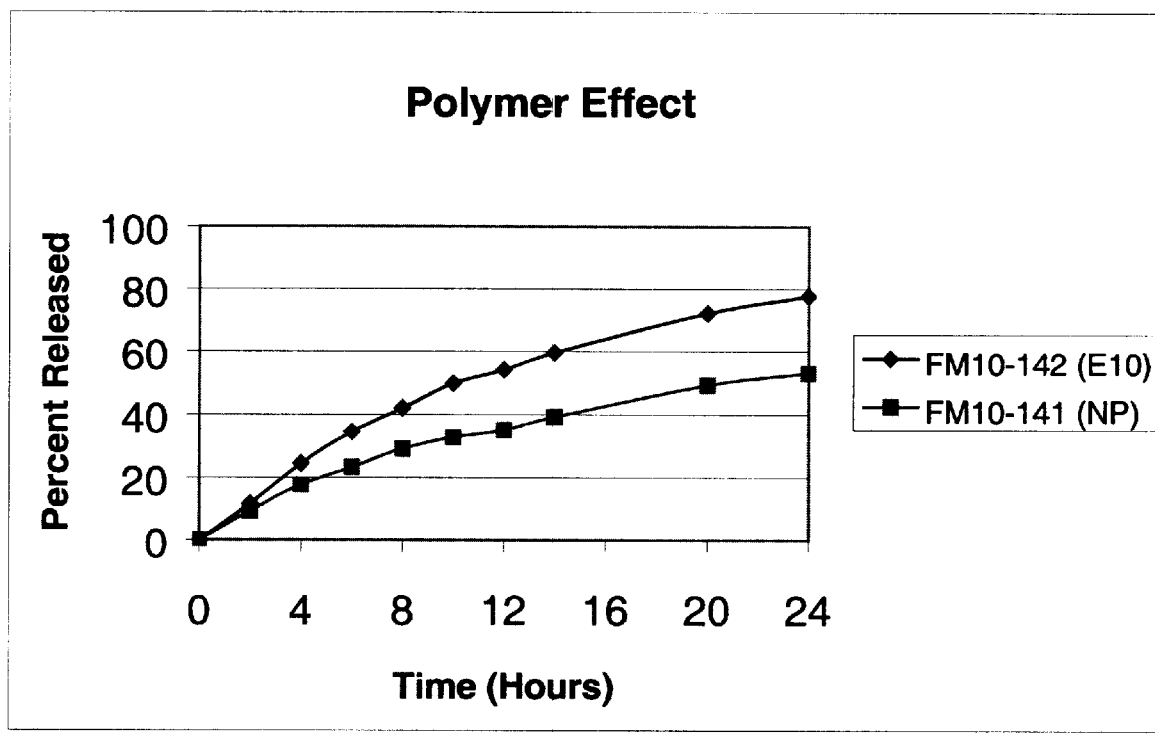
FIG. 8 is a graphical representation of the release of medicament in EXAMPLE 8 in terms of percent released with time.

Following the procedure of Example 7, using the amounts of the ingredients shown in Table 8, hard shell capsules of the formulations were obtained and the release of the medicament was determined by the procedure of Example 13. The results are shown graphically in FIG. 8 and show that the release of the medicament is sustained over 24 hours, the rate being higher for the formulation containing the cellulosic polymer, metocel E10P, that the formulation devoid of the cellulosic polymer. In FIG. 8, FM10-142 (E10), refers to Methocel E10P and FM10-141(NP), refers to a formulation without cellulosic polymer.

TABLE 8

| Formula/Ingredients | 1 | 2 |
|---|---|---|
| Niacin | 20.0 | 20.0 |
| Compritol 888 | 25.0 | 25.0 |
| Methocel E10 P | 3.0 | — |
| Olive Oil | 49.5 | 52.5 |
| Polysorbate 80 | 2.5 | 2.5 |

Example 9

Figure 9:
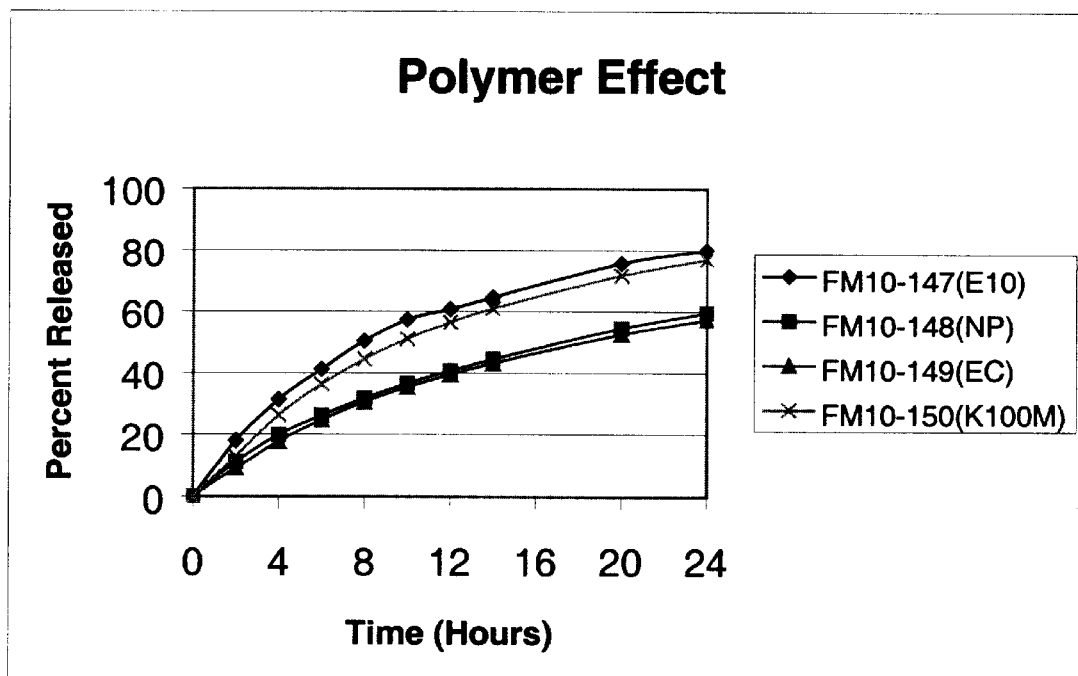
FIG. 9 is a graphical representation of the release of medicament in EXAMPLE 9 in terms of percent released with time.

The release of the medicament, caffeine, was determined by the procedure of Example 7, with the exception that the caffeine was first passed through a 120 mesh screen and particles greater than 200 mesh was discarded. The amounts of the components shown in Table 9 were used. The hard shell capsules were obtained and the release was determined by the procedure of Exarmple 13. The results are shown graphically in FIG. 9. The release of the medicament is sustained over a 24 hour period for each of the cellulosic polymers and for the formulation without a cellulosic polymer. The rate of release is dependent on the cellulosic polymer employed the rate being higher for the methocels than the ethocel, which is comparable to that of the formulation without a cellulosic polymer. In FIG. 9, FM10-147 (E10), refers to Methocel E10P, FM10-148 (NP) refers to a formulation without cellulosic polymer, FM10-140 (EC) refers to Ethocel P20 and FM10-150K (100M) refers to Methocel K100M.

TABLE 9

| Formula/Ingredients | 1 | 2 | 3 | 4 |
|---|---|---|---|---|
| Caffeine | 20.0 | 20.0 | 20.0 | 20.0 |
| Compritol 888 | 25.0 | 25.0 | 25.0 | 25.0 |
| Methocel E10 P | 3.0 | | | |
| Methocel K100M | | 3.0 | | |
| Ethocel P20 | | | 3.0 | |
| Olive Oil | 49.5 | 49.5 | 49.5 | 52.5 |
| Polysorbate 80 | 2.5 | 2.5 | 2.5 | 2.5 |

Example 10

Figure 10:
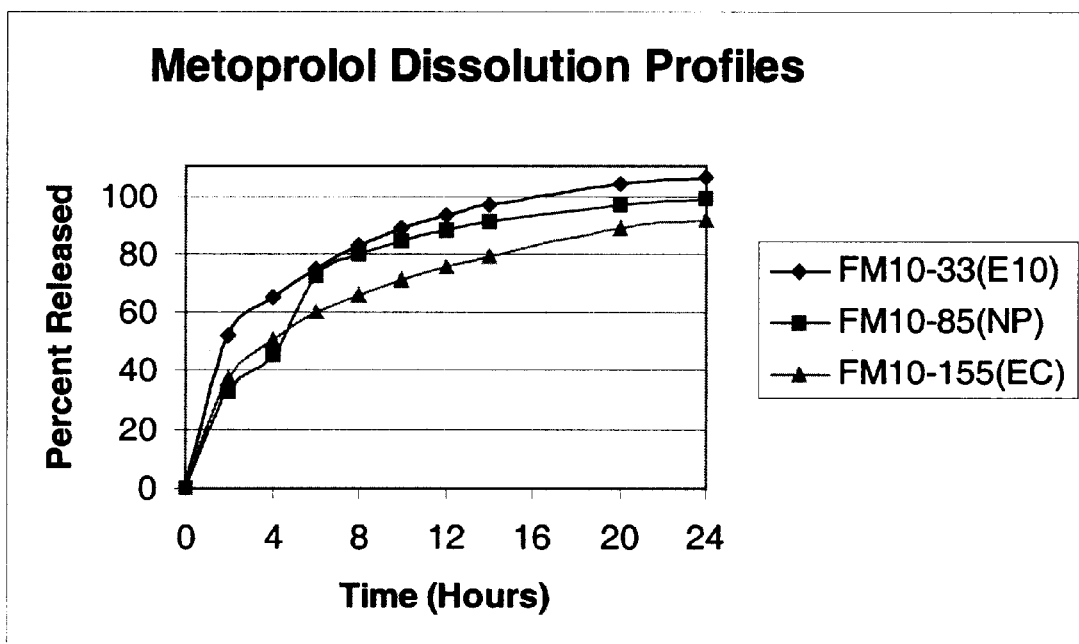
FIG. 10 is a graphical representation of the release of medicament in EXAMPLE 10 in terms of percent released with time.

Following the procedure of Example 7, using the amounts of the components shown in Table 10, hard shell capsules of the formulations were obtained. The capsules were formulated using various cellulosic polymers and the release of the medicament was determined by the procedure of Example 13. The results are shown graphically in FIG. 10 and demonstrate the sustained release of the medicament over a 24 hour period. In FIG. 10, FM10-33 (E10), refers to Methocel E10P, FM10-85 (NP) refers to a formulation without cellulosic polymer, FM10-155 (EC) refers to Ethocel P20.

TABLE 10

| Formula/Ingredients | 1 | 2 | 3 |
|---|---|---|---|
| Metoprolol Tartrate | 20.0 | 20.0 | 20.0 |
| Compritol 888 | 25.0 | 25.0 | 25.0 |
| Methocel E10 P | 3.0 | | |
| Ethocel P20 | | 3.0 | |
| Olive Oil | 51 | 51.0 | 54.0 |
| Polysorbate 80 | 2.5 | 2.5 | 2.5 |

Example 11

Figure 11:
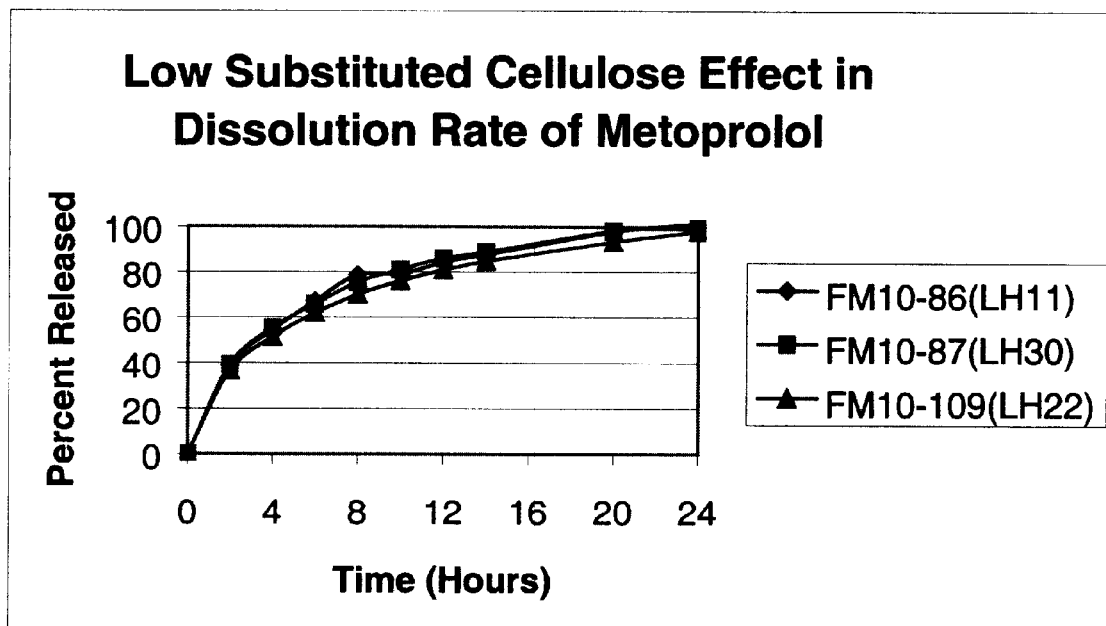
FIG. 11 is a graphical representation of the release of medicament in EXAMPLE 11 in terms of percent released with time.

Following the procedure of Example 7, using the amounts of the ingredients shown in Table 11, hard shell capsules of the formulations were obtained. The capsules were formulated using various cellulosic polymers and the release of the medicaments was determined by the procedure of Example 13. The results are shown graphically in FIG. 11 and demonstrate that the release of the active ingredient, metoprolol tartrate, is sustained over a 24 hour period, being essentially the same for each cellulosic polymer of the formulation. LH11, LH22 and LH30 refer to low hydroxypropyl ether cellulose LH11, LH22 and LH30, respectively. In FIG. 11, FM10-86 (LH11), FM10-87 (LH30) and FM10-109 (LH22) refer to low hydroxypropyl ether cellulose, respectively.

TABLE 11

| Formula/Ingredients | 1 | 2 | 3 |
|---|---|---|---|
| Metoprolol tartrate | 20.0 | 20.0 | 20.0 |
| Compritol 888 | 25.0 | 25.0 | 25.0 |
| LH 11 | 3.0 | | |
| LH 22 | | 3.0 | |
| LH 30 | | | 3.0 |
| Olive Oil | 51 | 51.0 | 51.0 |
| Polysorbate 80 | 1.0 | 1.0 | 1.0 |

Example 12

Figure 12:
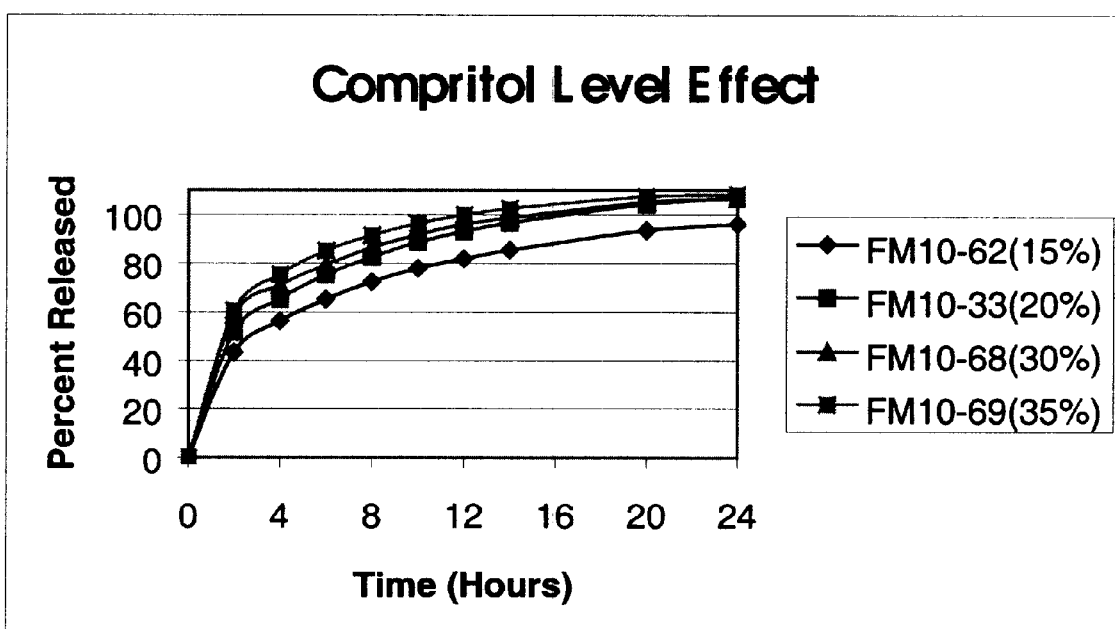
FIG. 12 is a graphical representation of the release of medicament in EXAMPLE 12 in terms of percent released with time.

Following the procedure of Example 7, using the amounts of the components shown in Table 12, hard shell capsules of the formulations were obtained. The capsules were formulated using various amounts of the high melting fatty acid ester, compritrol 888. The release of the medicament was determined by the procedure of Example 13. The results of the determination are shown graphically in FIG. 12 and demonstrate that the release of the medicament, metoprolol tartrate, is sustained over 24 hours. The release of the medicament is higher at the higher amounts of compritol. In FIG. 12, FM10-62 (15%), FM10-33 (20%), FM10-68(30%) and FM10-69 (35%) refer to formulations having 15%, 20% 30% and 35% of the total amount of the formulation of Compritol 888.

TABLE 12

| Formula/Ingredients | 1 | 2 | 3 | 4 |
|---|---|---|---|---|
| Metoprolol tartrate | 20.0 | 20.0 | 20.0 | 20.0 |
| Compritol 888 | 15.0 | 20.0 | 30.0 | 35.0 |
| Methocel E10 P | 3.0 | 3.0 | 3.0 | 3.0 |
| Olive Oil | 61 | 56.0 | 51.0 | 46.0 |
| Polysorbate 80 | 1.0 | 1.0 | 1.0 | 1.0 |

Example 13

In vitro Dissolution Procedure

The dissolution release of the formulations was determined by the USP Basket Method (Apparatus I). By this method, samples are tested in a 40 mesh basket rotating at 100 RPM. Release media were used in a volume of 900 ml per dissolution vessel, maintained at 37° C. Double distilled deionized water was generally used as the dissolution media. Some formulations were also evaluated in simulated gastric fluid (0.1N hydrochloric acid, pH=1.2, no enzyme added) or simulated intestinal fluid (0.05 M phosphate buffer, pH=7.4, no enzyme added). Nine samples of 3.0 ml each were automatically collected at 2, 4, 6, 10, 8, 12, 14, 20 and 24 hours. The absorbency of the samples were measured at the peak wavelength in the ultraviolet spectrum with Hewliet Packard model 8453 spectrophotometer. The absorbency values were converted to percentages of added medicament that was released.

We claim:

1. A sustained/prolonged release pharmaceutical unit dosage form comprising a hard shell capsule containing a formulation comprising:
   (a) a water soluble medicament selected from the group consisting of a pharmaceutically acceptable addition salt of hydroxyzine, a pharmaceutically acceptable addition salt of metoprolol, niacin, caffeine, theophylline, a pharmaceutically acceptable acid addition salt of diltiazem, a pharmaceutically acceptable acid addition salt of albuterol, a pharmaceutically acceptable acid addition salt of metformin, a pharmaceutically acceptable acid addition salt of metronidazole, a pharmaceutically acceptable acid addition salt of metochlopramide, a pharmaceutically acceptable acid addition salt of ranitidine, and a pharmaceutically acceptable acid addition salt of captopril;
   (b) a high melting fatty acid ester selected from the group consisting of glyceryl behenate, glyceryl palmitostearate and glyceryl stearate;
   (c) an oil selected from the group consisting of corn oil, cottonseed oil, menhaden oil, safflower oil, sesame oil, shark-liver oil, soybean oil, olive oil and wheat germ oil;
   (d) a cellulosic polymer selected from the group consisting of a low-substituted hydroxypropyl ether cellulose polymer and a cellulosic polymer having methylether substitution; and
   (e) a polysorbate 80 surfactant.

2. A pharmaceutical unit dosage form according to claim 1 wherein the high melting fatty acid ester comprises from about 10% to about 50% by weight of the total weight of the formulation.

3. A pharmaceutical unit dosage form according to claim 2 wherein the high melting fatty acid ester comprises from about 15% to about 35% by weight of the total weight of the formulation.

4. A pharmaceutical unit dosage form according to claim 3 wherein the high melting fatty acid ester comprises about 25% by weight of the total weight of the formulation.

5. A pharmaceutical unit dosage form according to claim 1 wherein the oil comprises about 40% to about 60% by weight of the total weight of the formulation.

6. A pharmaceutical unit dosage form according to claim 5 wherein the oil comprises about 50% by weight of the total weight of the formulation.

7. A pharmaceutical unit dosage form according to claim 1 wherein the cellulosic polymer comprises from about 1% to about 5% by weight of the total weight of the formulation.

8. A pharmaceutical unit dosage form according to claim 7 wherein the cellulosic polymer comprises from about 3% by weight of the total weight of the formulation.

9. A pharmaceutical unit dosage form according to claim 1 wherein the surfactant comprises about 1.0% to about 10% by weight of the total weight of the formulation.

10. A pharmaceutical unit dosage form according to claim 9 wherein the surfactant comprises from about 1% by weight of the total weight of the formulation.

11. A pharmaceutical unit dosage form according to claim 1 wherein the high melting fatty acid ester comprises from about 10% to about 50% by weight, the oil comprises about 46% to about 61% by weight, the cellulosic polymer comprises from about 1% to about 5% by weight and the surfactant comprises from about 1.0% to about 10% of the total weight of the formulation.

12. A pharmaceutical unit dosage form according to claim 11 wherein the higher melting fatty acid ester comprises from about 15% to about 35% by weight of the total weight of the formulation.

13. A pharmaceutical unit dosage form according to claim 12 wherein the higher melting fatty acid ester comprises about 25% by weight, the oil comprises about 51% by weight, the cellulosic polymer comprises about 3% by weight, and the surfactant comprises about 1% of the total weight of the formulation.

14. A pharmaceutical unit dosage form according to claim 1 wherein the water soluble medicament comprises about 20% by weight of the total weight of the formulation.

15. A pharmaceutical unit dosage form according to claim 1 wherein the high melting fatty acid ester comprises about 10% to about 50% by weight, the oil comprises from about 46% to about 61% by weight, the cellulosic polymer comprises from about 1% to about 5% by weight, and the surfactant comprises from about 1.0% to about 10% by weight, and the water soluble medicament comprises about 20% by weight of the total weight of the formulation.

16. A pharmaceutical unit dosage form according to claim 15 wherein the high melting fatty acid ester comprises about 25% by weight, the oil comprises about 51% by weight, the cellulosic polymer comprises about 3% by weight, and the surfactant comprises about 1.0% and the water soluble medicament comprises about 20% by weight of the total weight of the formulation.

17. A pharmaceutical composition comprising:
   (a) a high melting fatty acid ester selected from the group consisting of glyceryl behenate, glyceryl palmitostearate and glyceryl stearate;

(b) an oil selected from the group consisting of corn oil, cottonseed oil, menhaden oil, safflower oil, sesame oil, shark-liver oil, soybean oil, olive oil and wheat grain oil;

(c) a cellulosic polymer selected from the group consisting of a low substituted hydroxypropyl ether cellulosic polymer and a cellulosic polymer having methylether substitution; and (d) a surfactant comprising polysorbate 80.

18. A pharmaceutical unit dosage form according to claim 17 wherein the higher melting fatty acid ester comprises from about 10% to about 50% by weight of the total weight of the formulation.

19. A pharmaceutical formulation according to claim 18 wherein the high melting fatty acid ester comprises from about 15% to about 35% by weight of the total weight of the formulation.

20. A pharmaceutical formulation according to claim 19 wherein the high melting fatty acid ester comprises from about 25% by weight of the total weight of the formulation.

21. A pharmaceutical formulation according to claim 17 wherein the oil comprises about 46% to about 61% by weight of the total weight of the formulation.

22. A pharmaceutical formulation according to claim 21 wherein the oil comprises about 51% by weight of the total weight of the formulation.

23. A pharmaceutical formulation according to claim 17 wherein the cellulosic polymer comprises from about 1% to about 5% by weight of the total weight of the formulation.

24. A pharmaceutical formulation according to claim 23 wherein the cellulosic polymer comprises from about 3% by weight of the total weight of the formulation.

25. A pharmaceutical formulation according to claim 17 wherein the high melting fatty acid ester comprises from about 10% to about 50% by weight, the oil comprises about 46% to about 61% by weight, the cellulosic polymer comprises from about 1% to about 5% by weight and the surfactant comprises from about 1.0% by weight of the total weight of the formulation.

26. A pharmaceutical formulation according to claim 17 wherein the high melting fatty acid ester comprises about 25% by weight, the oil comprises about 51% by weight, the cellulosic polymer comprises about 3% by weight, and the surfactant comprises from about 1.0% by weight of the total weight of the formulation.

27. A process for the preparation of a sustained/prolonged release pharmaceutical unit dosage form comprising the steps of:

(a) fluidizing a high melting fatty acid ester, (b) granulating the fluidized fatty acid ester with an oil, a cellulosic polymer, a surfactant and a water soluble medicament; and (c) transferring the fluidized granulate to a hard shell capsule.

28. A process according to claim 27 wherein the water soluble medicament is selected from the group consisting of a pharmaceutically acceptable addition salt of hydroxyzine, a pharmaceutically acceptable addition salt of metoprolol, niacin, caffeine, theophylline and a pharmaceutically acceptable acid addition salt of diltiazem, a pharmaceutically acceptable acid addition salt of albuterol, a pharmaceutically acceptable acid addition salt of metformin, a pharmaceutically acceptable acid addition salt of metronidazole, a pharmaceutically acceptable acid addition salt of metochlopramide, a pharmaceutically acceptable acid addition salt of ranitidine, and a pharmaceutically acceptable acid addition salt of captopril; the fatty acid ester is selected from the group consisting of glyceryl behenate, glyceryl palmitostearate and glycerylstearate; the oil is selected from the group consisting of corn oil, cottonseed oil, menhaden oil, safflower oil, sesame oil, shark-liver oil, soybean oil, olive oil and wheat germ oil; the cellulosic polymer is selected from the group consisting of a low substituted hydroxypropyl ether cellulosic polymer and a cellulosic polymer having methylether substitution; and the surfactant comprises polysorbate 80.

29. A process according to claim 27 wherein the high melting fatty acid ester is fluidized at a temperature in the range of about 75° to 80° C.

30. The process according to claim 27 wherein the fluidized granulate is transferred to a hard shell capsule at a temperature of about 70° C.

31. A pharmaceutical unit dosage form according to claim 1 wherein the hard shell capsule comprises hydroxypropyl methylcellulose.

32. A process according to claim 27 wherein the hard shell capsule comprises hydroxypropyl methylcellulose.

33. A modulated release pharmaceutical construct which comprises a matrix of a material comprising of (a) a high melting fatty acid ester, (b) an oil, (c) a cellulosic polymer and (d) a medicament.

34. The construct as defined in claim 33 wherein the matrix further comprises a surfactant added to said material.

35. The construct as defined in claim 33 wherein the matrix is formed from a mixture comprising said ester selected from the group consisting of glyceryl behenate, glyceryl palmitostearate and glyceryl stearate; said oil selected from the group consisting of corn oil, cottonseed oil, menhaden oil, safflower oil, sesame oil, shark-liver oil, soybean oil, olive oil and wheat grain oil; and said polymer selected from the group consisting of a low substituted hydroxypropyl ether cellulosic and a cellulosic polymer having methylether substitution.

36. The construct as defined in claim 35 wherein said mixture further comprises a surfactant comprising polysorbate 80.

37. A sustained release pharmaceutical composition comprising:

a construct comprising (a) a high melting fatty acid ester, (b) an oil, (c) a cellulosic polymer and (d) a medicament.

38. A sustained release/prolonged release pharmaceutical unit dosage form comprising:

(a) a hard shell capsule;

(b) a carrier construct having a matrix of a material comprising (a) a high melting fatty acid ester, (b) an oil, (c) a cellulosic polymer and (d) a medicament.

39. A process for preparing a sustained/prolonged release pharmaceutical unit dosage form, which comprises:

(a) fluidizing a carrier comprising (a') a high melting fatty acid ester, (b') an oil and (c') a cellulosic polymer to form a carrier solution;

(b) adding a water soluble medicament to said carrier solution to form a medicament solution; and (c) transferring said medicament solution to a hard shell capsule to solidify said medicament solution to form the dosage form.

* * * * *